United States Patent
Stewart et al.

(10) Patent No.: US 10,358,442 B2
(45) Date of Patent: Jul. 23, 2019

(54) 2-HOMOPIPERAZINE-1-YL-4H-1,3-BENZOTHIAZINE-4-ONE DERIVATIVES AND PROCESS FOR THE PREPARATION OF 2-(HOMO)PIPERAZINE 1,3-BENZOTHIAZINE-4-ONE HYDROCHLORIDES

(71) Applicant: Ecole Polytechnique Federale De Lausanne (EPFL), Lausanne (CH)

(72) Inventors: Cole Stewart, Ecublens (CH); Vadim Albertovich Makarov, Moscow (RU)

(73) Assignee: ECOLE POLYTECHNIQUE FEDERALE DE LAUSANNE (EPFL) (CH)

(*) Notice: Subject to any disclaimer, the term of this patent is extended or adjusted under 35 U.S.C. 154(b) by 0 days.

(21) Appl. No.: 16/189,743

(22) Filed: Nov. 13, 2018

(65) Prior Publication Data

US 2019/0077798 A1 Mar. 14, 2019

Related U.S. Application Data

(62) Division of application No. 15/560,771, filed as application No. PCT/EP2016/056371 on Mar. 23, 2016, now Pat. No. 10,160,754.

(30) Foreign Application Priority Data

Mar. 23, 2015 (EP) .................................... 15160267

(51) Int. Cl.
  *C07D 417/04* (2006.01)
  *C07D 281/02* (2006.01)
  *C07D 279/08* (2006.01)

(52) U.S. Cl.
  CPC ......... *C07D 417/04* (2013.01); *C07D 279/08* (2013.01); *C07D 281/02* (2013.01)

(58) Field of Classification Search
  CPC .................................................... C07D 417/04
  USPC ............................................................ 544/50
  See application file for complete search history.

(56) References Cited

U.S. PATENT DOCUMENTS 10,160,754 B2  12/2018  Stewart et al.

FOREIGN PATENT DOCUMENTS

| WO | 2007/134625 A1 | 11/2007 | |
|---|---|---|---|
| WO | 2009/010163 A1 | 1/2009 | |
| WO | 2012/066518 A1 | 5/2012 | |
| WO | 2012/085654 A1 | 6/2012 | |
| WO | WO-2013185507 A1 * | 12/2013 | ........... C07D 279/08 |

OTHER PUBLICATIONS

Peng et al., Synthesis and antitubercular evaluation of 4-carbonyl piperazine substituted 1,3-benzothiazin-4-one derivatives. Bioorg Med Chem Lett. Apr. 1, 2015;25(7)1373-6. With Supplementary Information published Mar. 2, 2015, 25 pages.

* cited by examiner

*Primary Examiner* — Kahsay Habte

(74) *Attorney, Agent, or Firm* — McCarter & English, LLP; Jill Ann Mello

(57) ABSTRACT

2-homopiperazine-1-yl-4H-1, 3-bensothiazine-4-one derivatives of formula (I) are provided. They are useful in the treatment of bacterial infections, in particular tuberculosis, buruli ulcer and leprosy. A process for the preparation of 2-(homo)piperazine 1, 3-benzothiazine-4-one hydrochlorides is also provided.

9 Claims, No Drawings

2-HOMOPIPERAZINE-1-YL-4H-1,3-BENZOTHIAZINE-4-ONE DERIVATIVES AND PROCESS FOR THE PREPARATION OF 2-(HOMO)PIPERAZINE 1,3-BENZOTHIAZINE-4-ONE HYDROCHLORIDES

RELATED APPLICATIONS

This application is a Division of U.S. application Ser. No. 15/560,771, filed on Sep. 22, 2017; which is a national stage filing under 35 U.S.C. § 371 of International Application No. PCT/EP2016/056371, filed on Mar. 23, 2016; which claims priority to European Patent Application No. 15160267.9, filed on Mar. 23, 2015. The entire contents of each of the aforementioned applications are incorporated herein by reference.

TECHNICAL FIELD

The present invention relates to 2-homopiperazine-1-yl-4H-1,3-benzothiazine-4-one derivatives and their use in a method for treating mammalian infections caused by bacteria, especially tuberculosis (TB), buruli ulcer and leprosy. In another embodiment, the present invention relates to a process for the preparation of 2-(homo)piperazine-1,3-benzothiazine-4-one hydrochlorides.

BACKGROUND

Mycobacteria have plagued humanity for several millennia by causing major diseases like tuberculosis (TB), leprosy and Buruli ulcer. In terms of disease burden and mortality, TB is incontestably the most important and challenging threat to human health, in part because of the increasing prevalence of primary resistance to the current drugs. There is thus a growing need for new compounds with a novel mode of action (Balganesh, T. S., P. M. Alzari, and S. T. Cole. Trends Pharmacol Sci, 2038. 29(11): p. 576-81.) and these may also find application in treating other mycobacterial diseases and infections due to other Corynebacterineae. Leprosy is nearing elimination as a public health problem (Britton, W. J. and D. N. Lockwood. Lancet, 2004, 363(9416): p. 1209-19), thanks to the control measures implemented by the World Health Organisation, while the emerging disease, Buruli ulcer, is of growing concern (Demangel, C., T. P. Stinear, and S. T. Cole. Nat Rev Microbiol, 2009. 7(1): p. 50-60).

In the past twenty years, drug-resistant tuberculosis has reached an alarming level. In the 1990s, there had been increasing concern about the multidrug-resistant (MDR) form, where *Mycobacterium tuberculosis* has acquired resistance to the main front-line drugs, i.e. isoniazid and rifampicin. There are an estimated 500,000 cases of MDR-TB worldwide of which ~70,000 occur in Europe (Zignol, M. et al. J Infect Dis, 2006. 194: 479-485; Fears, R. S. Kaufmann, V. Ter Meulen & A. Zumla. Tuberculosis (Edinb) 2010. 90: 182-187).

In the past decade, MDR-strains of *M. tuberculosis* have acquired additional resistance mutations to second line drugs giving rise to extensively drug-resistant (XDR) disease. In addition to isoniazid and rifampicin, XDR strains of *M. tuberculosis* are also resistant to fluoroquinolones and to the injectable aminoglycosides (Jassal, M. & W. R. Bishai. Lancet Infect Dis 2009. 9: 19-30). Over 50 countries have now reported XDR-TB, thereby underlining the necessity and importance of finding new drugs to treat both drug-sensitive and drug-resistant TB. In addition to a new mechanism of action, a new TB drug advantageously exhibits high potency, so that treatment duration can be reduced; and high specificity, so that side-effects including destruction of the gut flora can be avoided. Preferably, the new drug is suitable for oral administration.

2-Amino substituted 1,3-benzothiazine-4-ones can be used as drugs for the treatment of mycobacterial diseases in humans and mammals. Presently, the most active compounds available are 2-[(2S)-2-methyl-1,4-dioxa-8-azaspiro[4.5]dec-8-yl]-8-nitro-6-(trifluoromethyl)-4H-1,3-benzo-thia-zin-4-one (BTZ043) (V. Makarov et al. *Science*, 2009, 324, 801; M. R. Pasca, et al. *Antimicrob, Agents Chemother.*, 2010, 54, 1616) and 2-[4-(cyclohexylmethyl)piperazin-1-yl]-8-nitro-6-(trifluoromethyl)-4H-1,3-benzothiazin-4-one (PBTZ169) (V. Makarov et al. *EMBO Mol Med.* 2014, 6(3):372-83).

It is thus desirable to provide drugs effective in the treatment of mammalian infections caused by bacteria, especially disease such as tuberculosis, Buruli ulcer and leprosy with an improved inhibitory activity. Preferably, these drugs are effective against MDR- and XDR-strains as well as strains which are resistant against other drugs.

Recent methods for the synthesis of 2-amino substituted 1,3-benzothiazine-4-ones are described e.g. in WO 2007/134625, WO 2009/010163 and EP 2 029 533. These methods include:
1) Reacting 2-chlorobenzcarboxamide with a substituted piperazine sodium dithiocarbamate (e.g. WO 2009/010163, method A to C).

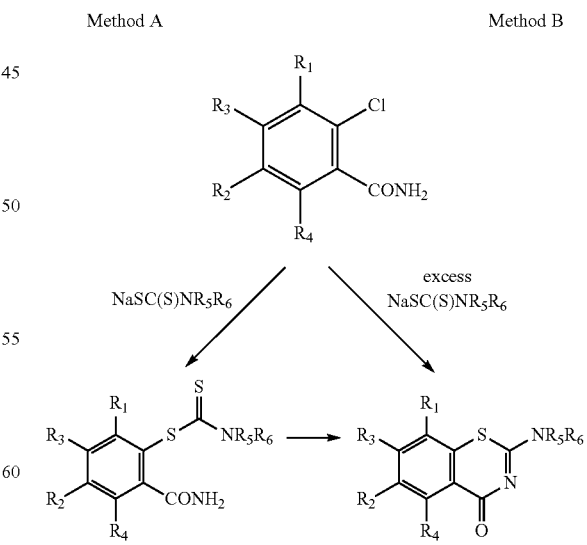

This reaction results in the formation of free $H_2S$, which can result in undesirable side products, thereby negatively influencing purity and yield.

2) Reacting 2-chlorobenzcarboxamide with a metal alkylxantogenate. The isolated 2-alkoxy-4H-1,3-benzothiazine-4-one is further reacted with a secondary amine (WO 2009/01063).

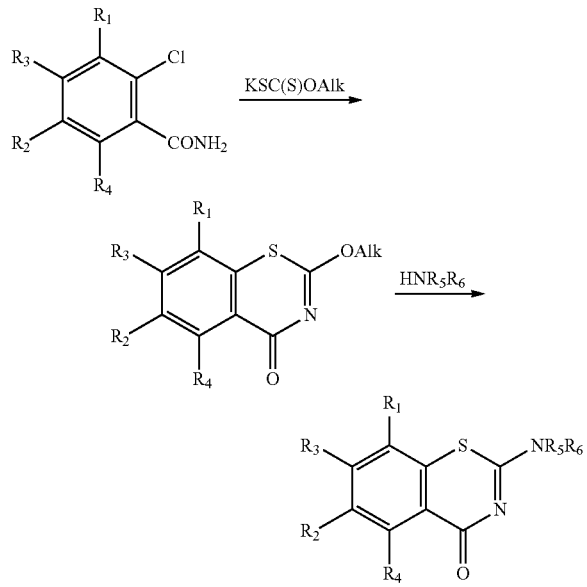

The reaction is a two-step reaction which necessitates isolation of the intermediate Product.

3) Reacting 2-chlorobenzoyl chloride (e.g. WO 2009/010163, method D) with a thiocyanate salt and subsequently treating the crude 2-chlorobenzoylthicoyanate with the corresponding secondary amine (EP 2 029 583). In this method, the yield of the final product is in the range of below 1% which is unsatisfactory and unsuitable for industrial application.

In view of these drawbacks, it is highly desirable to provide a process for preparing 2-amino-substituted 1,3-benzothiazine-4-ones, especially 2-(homo)piperazine-1,3-benzothiazine-4-one derivatives which is superior to the prior art methods and which is suitable for manufacture in an industrial scale.

It has surprisingly been found that 2-(homo)piperazine 1,3-benzothiazine-4-one hydrochlorides of general formula (Ia) can be obtained in a high yield by (1) reaction of 2-chloro-3-nitro-5-(trifluoromethyl)benzoyl chloride of general formula (II) with a thiocyanate salt M-SCN, (2) followed by reaction with a 2-substituted piperazine or homopiperazine, and (3) acidification with hydrochloric acid.

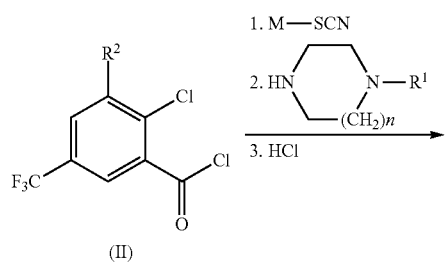

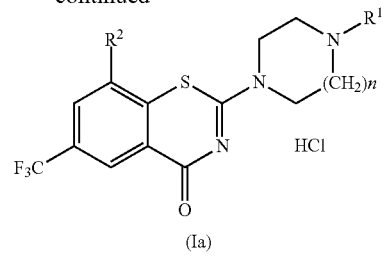

By way of this process, the hydrochlorides of general formula (Ia) are obtained in high yields (58%-78%) and high purity in a one pot-reaction. This finding was very surprising because it was known from the prior art that the reaction of piperidine derivatives with an isothiocyanate results in very low yields of below 1% (see EP 2 029 583).

SUMMARY OF THE INVENTION

Consequently, the present invention relates to a process for the preparation of 2-(homo)piperazine (diazepan) 1,3-benzothiazine-4-one hydrochlorides of general formula (Ia) which comprises the following steps:

(1) reacting a substituted 2-chloro-5-(trifluoromethyl)benzoyl chloride of formula (II) with a thiocyanate salt M-SCN;

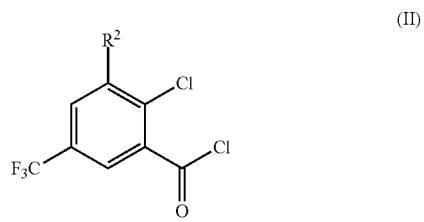

(2) reacting the resulting substituted 2-chloro-5-(trifluoromethyl)benzoyl isothiocyanate without isolation with a substituted piperazine or homopiperazine of formula (III);

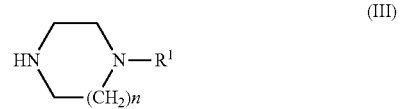

(3) acidifying the resulting 2-(homo)piperazine-1,3-benzothiazine-4-one with hydrochloric acid to obtain a compound of formula (Ia).

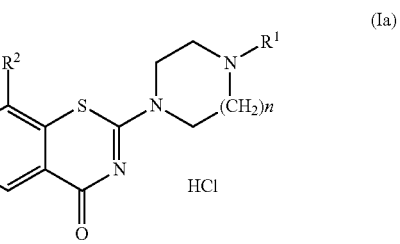

wherein n is 1 or 2; preferably 2;

$R^1$ is a linear, branched or cyclic $C_{3-12}$ alkyl group, a linear, branched or cyclic $C_{3-12}$ alkenyl group or a linear or branched $C_{3-12}$ alkynyl group, all of which may be substituted with halogen (such as F, Cl, Br and I), and wherein one or two $CH_2$-groups may be substituted with O or S, or

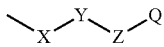

wherein

X is a linear or branched $C_{1-6}$ alkyl group, a linear or branched $C_{1-6}$ alkenyl group or a linear or branched $C_{1-6}$ alkynyl group;

Y is a direct bond, O, S, NH, NMe, NEt, or NPr;

Z is a direct bond, or a linear or branched $C_{1-3}$ alkyl group;

Q is cyclopentyl, cyclohexyl, cycloheptyl, phenyl, or naphtyl, which may be substituted with 1-3 substituents selected from halogen, a linear or branched $C_{1-3}$ alkoxy group, a linear or branched $C_{1-3}$ alkenyloxy group, a linear or branched $C_{1-3}$ alkynyloxy group, mono-, di or trifluoromethyl;

M is an alkali metal, or $NH_4$; preferably Na, K or $NH_4$; more preferably $NH_4$;

$R^2$ is $NO_2$, NHOH; preferably $NO_2$.

In a second aspect, the present invention is directed to 2-homopiperazine-1-yl-4H-1,3-benzothiazine-4-one derivatives according to general formula (I) and their pharmaceutically acceptable salts, in particular to their hydrochlorides.

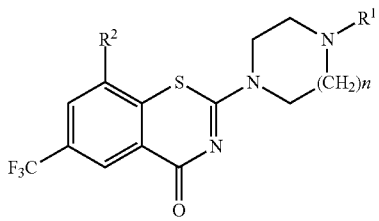

(I)

wherein n is 2;

$R^1$ s a linear, branched or cyclic $C_{3-12}$ alkyl group, a linear, branched or cyclic $C_{3-12}$, alkenyl group, a linear, branched or cyclic $C_{3-12}$ alkynyl group, all of which may be substituted with halogen (such as F, Cl, Br and I), and wherein one or two $CH_2$-groups may be substituted with O or S, or

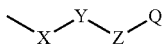

wherein

X is a linear or branched $C_{1-6}$ alkyl group, a linear or branched $C_{1-6}$ alkenyl group, or a linear or branched $C_{1-6}$ alkynyl group;

Y is a direct bond, O, S, NH, NMe, NEt, or NPr;

Z is a direct bond, or a linear or branched $C_{1-3}$ alkyl group;

Q is cyclopentyl, cyclohexyl, cycloheptyl, phenyl, or naphtyl, which may be substituted with 1-3 substituents selected from halogen, a linear or branched $C_{1-3}$ alkoxy group, a linear or branched $C_{1-3}$ alkenyloxy group, a linear or branched $C_{1-3}$ alkynyloxy group, mono-, di or trifluoromethyl; and $R^2$ is $NO_2$ or NHOH; preferably $NO_2$.

DETAILED DESCRIPTION OF THE INVENTION

In a first aspect, the present invention provides a one-pot synthesis for the preparation of 2-piperazine and 2-homopiperazine 1,3-benzothiazine-4-one hydrochlorides of general formula (Ia). The term "homopiperazine" is synonymous with the term "diazepan" and can be used interchangeably.

As the process of the present invention is a one-pot-synthesis, it is unnecessary to isolate and purify the intermediates which may be difficult and usually lowers the yield of the final product.

The process according to the invention comprises the following steps:

(1) reacting a substituted 2-chloro-5-(trifluoromethyl)benzoyl chloride of formula (II) with a thiocyanate salt M-SCN;

(2) reacting the resulting substituted 2-chloro-5-(trifluoromethyl)benzoyl isothiocyanate without isolation with a substituted piperazine or homopiperazine of formula (III);

(3) acidifying the resulting 2-piperazine or 2-homopiperazine 1,3-benzothiazine-4-one with hydrochloric acid to obtain a compound of formula (Ia).

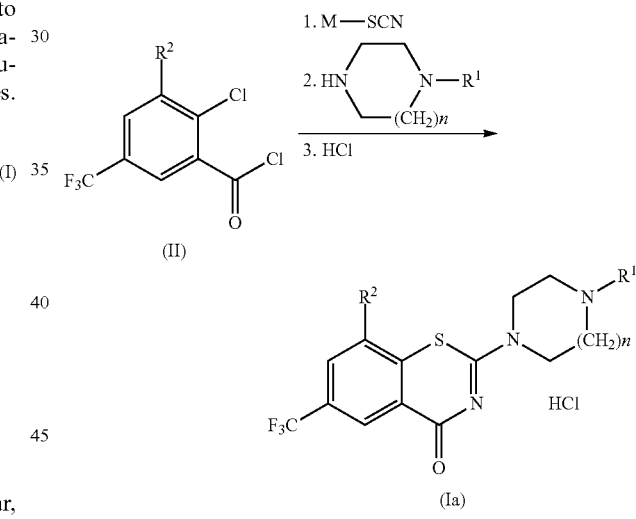

In this scheme, n, $R^1$, M, and $R^2$ are as defined above. Preferred embodiments of $R^1$ and $R^2$ are those which are described below in relation to the compounds of the invention.

The compounds wherein $R^2$ is NHOH may be obtained by reducing the corresponding compound of formula (Ia) wherein $R^2$ is $NO_2$ in a manner known to the skilled person.

The hydrochlorides of general formula (Ia) which are obtained in the process of the present invention may be converted into the corresponding compounds of general formula (I), i.e. into the free base form or other pharmaceutically acceptable salts thereof, by standard methods which are known to the skilled person. In particular, the free base may conveniently be obtained by reaction of the hydrochloride salt with sodium carbonate.

The process of the present invention, is preferably carried out in an organic solvent, preferably THF or acetone, most preferably THF.

Hereinafter, a particularly preferred embodiment of the process according to the invention is described:

In the first reaction step, a solution of a substituted 2-chloro-5-(trifluoromethyl)benzoyl chloride in THF, preferably 2-chloro-3-nitro-5-(trifluoromethyl)benzoyl chloride, is added to a solution of the thiocyanate salt M-SCN at a temperature of −10° C. to +30° C., preferably −5 to +20° C.

In this step, the thiocyanate salt. M-SCN is preferably used in a molar ratio of from 1 to 3, more preferably of from 1 to 1.4, based on the compound of formula (II).

Following the reaction of the thiocyanate salt with the substituted 2-chloro-5-(trifluoromethyl)benzoyl chloride so as to obtain the corresponding 2-chloro-5-(trifluoromethyl) benzoyl isothiocyanate, the precipitated, white, solid alkali/ammonium chloride is removed by filtration.

In the second reaction step, a freshly distilled substituted piperazine or homopiperazine in THF is added dropwise to the substituted 2-chloro-5-(trifluoromethyl)benzoyl isothiocyanate mother liquid at a temperature of −10° C. to +75° C., preferably between 0 to +50° C. The free base of the 2-piperazine or 2-homopiperazine 1,3-benzothiazine-4-one precipitates as a solid from the reaction mixture during storage at a temperature of between 0° C. to +30° C., preferably at +25° C., for 0.5 to 3 hours.

The substituted piperazine or homopiperazine is used in a molar ratio of 1 to 5, preferably in a molar ratio of 1 to 2, based on the compound of formula (IT).

In the final acidification step, the obtained reaction mixture is treated with a solution of HCl in water or an organic solvent, preferably methanol, ethanol, isopropanol or ethyl acetate, thereby converting the free base into the hydrochloride salt. The hydrochloride salt precipitates from the reaction mixture, and is obtained with high yield and purity.

Preferably, HCl is used in a concentration of 5%, and is added in an amount so as to adjust the pH to about 2. The mixture is cooled over night, preferably at a temperature of 4° C. The precipitated 2-piperazine or 2-homopiperazine 1,3-benzothiazine-4-one hydrochloride is filtered off, and subsequently washed with a small amount of an organic solvent, preferably acetone.

In a second embodiment, the present invention is directed to novel 2-piperazine-1-yl-4H-1,3-benzothiazine-4-one derivatives of formula (I) and their pharmaceutically acceptable salts, in particular to the hydrochloride salts of the compounds of formula (I):

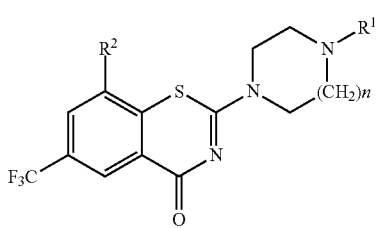

(I)

wherein n, $R^1$, and $R^2$ are as defined above.

In a preferred embodiment, $R^1$ is a linear, branched or cyclic $C_{3-12}$ alkyl group which may be substituted with halogen and wherein one or two $CH_2$-groups may be substituted with O or S. In a more preferred embodiment, $R^1$ is a linear, branched or cyclic $C_{3-12}$ alkyl group, wherein one $CH_2$-group may be substituted with O. In an even more preferred embodiment, $R^1$ is a linear, branched or cyclic $C_{4-9}$ alkyl group, wherein one $CH_2$ group may be substituted with O. In the most preferred embodiment, $R^1$ is a linear or cyclic $C_{4-9}$ alkyl group.

In a particularly preferred embodiment of the compounds of formula (I), $R^1$ is a linear or cyclic $C_{4-9}$ alkyl group and $R^2$ is $NO_2$.

The compounds of formula (I) may be in the form of their free bases or their pharmaceutically acceptable salts, including their hydrochlorides, sulfates, nitrates, methanesulfonates, benzenesulfonates, oxalates, maleates, phosphates, malates, tartrates, fumarates and salicylates, preferably their hydrochlorides and sulfates. The hydrochlorides are particularly preferred.

The compounds of the formula (I) according to the invention exhibit strong antibacterial activity, especially against mycobacteria with minimal inhibitory concentrations (MIC) in the range of ~0.2-1 ng/ml for *M. tuberculosis* H37Rv, determined by the resazurin reduction method (J. C. Palomino, A. Martin, M. Camacho, H. Guerra, J. Swings, F. Portaels, *Antimicrob, Agents Chemother.*, 2002, 46, 2720-2722). In particular, the compounds according to the invention demonstrate a high level of selectivity for mycobacteria and related actinobacteria, so that they are expected to be associated with fewer adverse effects.

Thus, the compounds of the invention are useful for the treatment of mycobacterial infections, and even other actinobacterial infections such as diphtheria or nocardiosis, in humans and in animals. They are especially potent in the treatment of tuberculosis, buruli ulcer and leprosy.

Pharmaceutical compositions comprising the compounds according to the invention may be prepared in a manner known to the skilled person, e.g. by mixing with commonly used excipients and tabletelting.

The present invention will hereinafter be described in more detail by way of the following non-limiting examples.

EXAMPLES

Chemicals and solvents were purchased from Alfa-Aesar (GB) or from Aldrich Co. (Sigma-Aldrich Company, St-Louis, US). They were used without additional purification.

Melting points were determined according to the EP procedure and are uncorrected (Electrothermal 9001, GB).

The molecular formula was analysed (Carlo-Erba 5500, Italy).

NMR spectra were determined with a Varian Unity Plus 300 (USA). Shifts for $^1H$ NMR are reported in ppm downfield from TMS (δ).

Mass spectra were obtained using a Finnigan SSQ-700 (USA) instrument with direct injection.

Reactions and purity of compounds were controlled by TLC using Silicagel 60 $F_{254}$ aluminium sheets (Merck Co, Germany).

Example 1

2-[4-(Cyclohexylmethyl)-1,4-diazepan-1-yl]-8-nitro-6-(trifluoromethyl)-4H-1,3-benzothiazin-4-one Hydrochloride (Compound 1)

A solution of 5.0 g (17.3 mmol) fresh 2-chloro-3-nitro-5-(trifluoromethyl)benzoyl chloride in 25 ml of THF was added to a solution of 1.45 g (19.0 mmol) NH$_4$SCN in 25 ml of THE within 5 rain at room temperature. The reaction mixture was stored for 10 min at room temperature, and the white solid (NH$_4$Cl) was quickly removed by filtration, and washed with 5 ml THF. A solution of 3.40 g (17.3 mmol) of distilled 1-(cyclohexylmethyl)-1,4-diazepane in 25 THF was added dropwise to the mother liquid within 5 min at room temperature and a yellow solid formed. The reaction mixture was stored for 1 hour at room temperature, and subsequently treated with 5% HCl solution in MeOH until a pH of ~2 was reached. The mixture was cooled to 4° C. overnight. Light yellow 2-[4-(cyclohexylmethyl)-1,4-diazepan-1-yl]-8-nitro-6-(trifluoromethyl)-4H-1,3-benzothiazin-4-one was filtered off and washed with a small volume of acetone.

The product was recrystallized from an appropriate solvent, such as EtOH.

Yield: 67%
mp: 269-271° C. (EtOH)
MS (m/z): 470 (M$^+$)
$^1$H NMR (DMSO-d$_6$): δ10.93 (1H, broad s, NH), 8.80 and 8.86 (two 1H, two s, 2CH), 4.60 and 4.32 (2H, broad s, NC$\underline{H}_2$), 3.78 (2H, broad s, NHC$\underline{H}_2$), 3.16 (2H, broad s, NC$\underline{H}_2$), 3.18 (2H, broad s, NC$\underline{H}_2$), 2.96 (2H, broad s, CH$_2$), 2.12 (2H, broad s, NC$\underline{H}_2$), 1.86 (2H, broad s, CH$_2$), 1.74 and 1.55 (11H, 2 m. HC(CH$_2$)$_5$) ppm
Anal. for C$_{21}$H$_{25}$F$_3$N$_4$O$_3$S×HCl:
Calc.: C, 49.75; H, 5.17; N, 11.05.
Found: C, 49.64; H, 5.14; N, 11.14.

The following compounds were obtained by conducting the process of Example 1, except for using the appropriate (homo)piperazine derivative.

Example 2

8-Nitro-2-(4-pentyl-1,4-diazepan-1-yl)-6-(trifluoromethyl)-4H-1,3-benzothiazin-4-one Hydrochloride (Compound 2)
Yield: 59%
mp: 246-248° C. (EtOH)
MS (m/z): 444 (M$^+$)
$^1$H NMR (DMSO-d$_6$): δ 10.89 (1H, broad s, NH), 8.82 and 8.86 (two 1H, two s, 2CH), 0.76-4.62 (21H, several very broad s, CH$_2$ and CH$_3$) ppm
Anal. for C$_{19}$H$_{23}$F$_3$N$_4$O$_3$S×HCl:
Calc.: C, 47.45; H, 5.29; N, 11.32.
Found: C, 47.47; H, 5.26; N, 11.30.

Example 3

2-(4-Hexyl-1,4-diazepan-1-yl)-8-nitro-6-(trifluoromethyl)-4H-1,3-benzothiazin-4-one Hydrochloride (Compound 3)
Yield: 63%
mp: 249-251° C. (EtOH)
MS (m/z): 458 (M$^+$)
$^1$H NMR (DMSO-d$_6$): δ 10.92 (1H, broad s, NH), 8.81 and 8.87 (two 1H, two s, 2CH), 4.64 and 4.21 (2H, broad d, NHC$\underline{H}_2$), 3.92 (2H, broad s, NC$\underline{H}_2$), 3.65 (2H, broad s, NC$\underline{H}_2$), 3.06 (2H, broad s, NC$\underline{H}_2$), 2.32 (2H, broad s, NC$\underline{H}_2$), 1.76 (2H, broad s, C$\underline{H}_2$), 1.35 (6H, broad s, (CH$_2$)$_3$) and 0.94 (2H, broad s, CH$_2$) ppm Anal. for C$_{20}$H$_{25}$F$_3$N$_4$O$_3$S×HCl:
Calc.: C, 48.53; H, 5.29; N, 11.32.
Found: C, 48.59; H, 5.23; N, 11.27.

Example 4

2-[4-(2-Cyclohexylethyl)-1,4-diazepan-1-yl]-8-nitro-6-(trifluoromethyl)-4H-1,3-benzothiazin-4-one Hydrochloride (Compound 4)
Yield: 60%
mp: 274-277° C. (EtOH)
MS (m/z): 484 (M$^+$)
$^1$H NMR (DMSO-d$_6$): δ 10.86 (1H, broad s, NH), 8.82 and 8.86 (two 1H, two s, 2CH), 0.91-4.65 (25H, several very broad s, 12 CH$_2$ and CH) ppm
Anal. for C$_{22}$H$_{27}$F$_3$N$_4$O$_3$S×HCl:
Calc.: C, 50.72; H, 5.42; N, 10.75.
Found: C, 50.75; H, 5.59; N. 10.59.

Example 5

2-(4-Heptyl-1,4-diazepan-1-yl)-8-nitro-6-(trifluoromethyl)-4H-1,3-benzothiazin-4-one Hydrochloride (Compound 5)
Yield: 67%
mp: 256-258° C. (EtOH)
MS (m/z): 472 (M$^+$)
$^1$H NMR (DMSO-d$_6$): δ 10.85 (1H, broad s, NH), 8.81 and 8.87 (two 1H, two s, 2CH), 1.12-4.68 (25H, several very broad s, 11 CH$_2$ and CH$_3$) ppm
Anal. for C$_{21}$H$_{27}$F$_3$N$_4$O$_1$S×HCl:
Calc.: C, 49.55; H, 5.54; N, 11.01.
Found: C, 49.47; H, 5.50; N, 11.09.

Example 6

2-(4-Cyclohexyl-1,4-diazepan-1-yl)-8-nitro-6-(trifluoromethyl)-4H-1,3-benzothiazin-4-one Hydrochloride (Compound 6)
Yield: 64%
mp: 290-293° C. (EtOH/H$_2$O)
MS (m/z):456 (M$^+$)
$^1$H NMR (DMSO-d$_6$): δ 10.89 (1H, broad s, NH), 8.82 and 8.87 (two 1H, two s, 2CH), 0.87-4.65 (21H, several very broad s, 10 CH$_2$ and CH) ppm
Anal. for C$_{20}$H$_{24}$F$_3$N$_4$O$_3$S×HCl:
Calc.: C, 48.73; H, 4.91; N, 11.37.
Found: C, 48.66; H, 4.94; N, 11.42.

Example 7

8-Nitro-2-[4-(2-phenylethyl)-1,4-diazepan-1-yl]-6-(trifluoromethyl)-4H-1,3-benzothiazin-4-one Hydrochloride (Compound 7)
Yield: 58%
mp 264-267° C. (EtOH/H$_2$O)
MS (m/z): 478 (M$^+$)
$^1$H NMR (DMSO-d$_6$): δ 11.32 (1H, broad s, NH), 8.98 and 8.89 (two 1H, two s, 2CH), 7.21-7.43 (5H, m, C$_6$H$_5$), 4.60 and 4.34 (2H, broad d, NHC$\underline{H}_2$), 4.01 (2H, broad s, N CH$_2$), 3.65 (2H, broad s, NCH$_2$), 3.32 (2H, broad s, NCH$_2$), 3.13 (2H, broad s, CH$_2$), 2.61 (2H, broad s, CH$_2$), 2.40 (2H, broad s, NHCH$_2$) ppm Anal. for C$_{22}$H$_{21}$F$_3$N$_4$O$_3$S×HCl:
Calc.: C, 51.31; H, 4.31; N, 10.88.
Found: C, 51.37; H, 4.37; N, 10.93.

Example 8

Synthesis of 2-[4-(cyclohexylmethyl)piperazin-1-yl]-8-nitro-6-(trifluoromethyl)-4H-1,3-benzothiazin-4-one Hydrochloride Hydrochloride (PBTZ169×HCl)

(Compound 8)
Yield: 78%
mp: 296-297° C. (EtOH/H$_2$O)
MS (m/z): 456 (M$^+$)
$^1$H NMR (DMSO-d$_6$): δ 11.13 (1H, broad s, NH), 8.86 and 8.76 (two 1H, two s, 2CH), 4.64 (2H, broad s, NHCH$_2$), 3.94 (2H, broad s, NHCH$_2$), 3.18 (2H, broad s, NCH$_2$), 3.18 (2H, broad s, NCH$_2$), 2.96 (2H, broad s, CH$_2$), 1.75 and 1.53 (11H, 2 m, HC(CH$_2$)$_5$) ppm Anal. for C$_{20}$H$_{23}$F$_3$N$_4$O$_3$S×HCl:
Calc.: C, 48.73; H, 4.91; N, 11.37.
Found: C, 48.79; H, 4.85; N, 11.46.

The following compounds in the form of light yellow crystals were obtained in the same manner as Example 8.

Example 9

2-[4-(2-Cyclohexylethyl)piperazin-1-yl]-8-nitro-6-(trifluoromethyl)-4H-1,3-benzothiazin-4-one Hydrochloride (Compound 9)
Yield: 76.7%
mp: 271-273° C. (EtOH/H$_2$O)
MS (m/z): 470 (M$^+$)
$^1$H NMR (DMSO-d$_6$): δ 11.13 (1H, broad s, NH), 8.86 and 8.76 (two 1H, two s, 2CH), 3.91 (4H, broad s, N(CH$_2$)$_2$), 2.51 (4H, broad s, N(CH$_2$)$_2$), 2.36 (2H, t, CH$_2$), 1.70-0.85 (13H, 4 broad m, CH$_2$—CH(C$_5$H$_{10}$)) ppm.

Anal. for C$_{21}$H$_{25}$F$_3$N$_4$O$_3$S×HCl:
Calc.: C, 49.75; H, 5.17; N, 11.05.
Found: C, 49.63; H, 5.11; N, 11.20.

Example 10

2-(4-Heptylpiperazin-1-yl)-8-nitro-6-(trifluoromethyl)-4H-1,3-benzothiazin-4-one Hydrochloride (Compound 10)
Yield: 68%
mp: 254-256° C. (EtOH/H$_2$O)
MS (m/z): 458 (M$^+$)
$^1$H NMR (DMSO-d$_6$): δ 11.01 (1H, broad s, NH), 8.85 and 8.76 (two 1H, two 2CH), 3.90 (4H, broad s, N(CH$_2$)$_2$), 2.52 (4H, broad s, N(CH$_2$)$_2$), 2.33 (3H, t, CH), 1.43 (2H, broad m, CH$_2$), 1.28 (8H, broad m, 4CH$_2$) 0.86 (3H, t, CH$_3$) ppm Anal. for C$_{20}$H$_{25}$F$_3$N$_4$O$_3$S×HCl:
Calc.: C, 48.53; H, 5.29; N, 11.32.
Found: C, 48.61; H, 5.22; N, 11.18.

Example 11

8-Nitro-2-[4-(4-phenoxybutyl)piperazin-1-yl]-6-(trifluoromethyl)-4H-1,3-benzothiazin-4-one Hydrochloride (Compound 11)
Yield: 74%
mp: 256-258° C. (EtOH)
MS (m/z): 508 (M$^+$)
$^1$H NMR (DMSO-d$_6$): δ 10.93 (1H, broad s, NH), 8.91 and 8.80 (two 1H, two s, 2CH), 7.29 (2H, t, 2CH), 6.93 (3H, d, 3CH), 4.03 (2H, t, OCH$_2$), 3.65 (2H, d, 2CH), 3.19 (4H, broad m, N(CH$_2$)$_2$), 1.94 and 1.79 (4H, 2 broad m, 2CH$_2$) ppm Anal. for C$_{23}$H$_{23}$F$_3$N$_4$O$_4$S×HCl:
Calc.: C, 50.69; H, 4.44; N, 10.28.
Found: C, 50.47; H, 4.32; N, 10.16.

Example 12

2-(4-[3-(4-Fluorophenoxy)propyl]piperazin-1-yl)-8-nitro-6-(trifluoromethyl)-4H-1,3-benzothiazin-4-one Hydrochloride (Compound 12)
Yield: 77%
mp: 261-2637° C. (ethanol)
MS (m/z): 512 (M$^+$)
$^1$H NMR (DMSO-d$_6$): δ 10.97 (1H, broad s, NH), 8.85 and 8.76 (two 1□H, two s, 2CH), 7.11 (2H, t, 2CH), 6.94 (2H, m, 2CH), 4.12 (2H, t, OCH$_2$), 3.85 (4H, broad s, N(CH$_2$)$_2$), 2.52 (4H, broad s, N(CH$_2$)$_2$), 2.48 (2H, m, CH$_2$), 1.83 (2H, q, CH$_2$) ppm Anal. for C$_{22}$H$_{20}$F$_4$N$_4$O$_4$S×HCl:
Calc.: C, 48.14; H, 3.86; N, 10.21.
Found: C, 47.97; H, 3.83; N, 10.27.

Example 13

2-(4-Butylpiperazin-1-yl)-8-nitro-6-(trifluoromethyl)-4H-1,3-benzothiazin-4-one Hydrochloride (Compound 13)
Yield: 67%
mp: 239-241° C. (EtOH/H$_2$O)
MS (m/z): 416 (M$^+$)
$^1$H NMR (DMSO-d$_6$): δ 10.06 (1H, broad n, NH), 8.85 and 8.76 (two 1H, two s, 2CH), 3.90 (4H, broad s, N(CH$_2$)$_2$), 2.51 (4H, broad s, N(CH$_2$)$_2$), 2.32 (2H, t, CH$_2$), 1.46 and 1.33 (4H, 2 m, 2CH$_2$), 0.91 (3H, t, CH$_3$) ppm Anal. for C$_{17}$H$_{19}$F$_3$N$_4$O$_3$S×HCl:
Calc.: C, 45.09; H, 4.45; N, 12.37.
Found: C, 45.16; H, 4.54; N, 12.30.

Example 14

In Vitro Inhibitory Activity of the Compounds of the Invention Against Mycobacteria Activity against *M. tuberculosis* strains H37Rv and NBT1 was determined by the resazurin reduction assay (MIC$_{99}$). The method is described in detail in: J. C. Palomino, A. Martin, M. Camacho, H. Guerra, J. Swings, F. Portaels, Antimicrob. Agents Chemother., 2002, 46, 2720-2722. The results are presented in Table 1.

TABLE 1

| Compound | Units | H37Rv MIC$_{99}$ | NTB1 MIC$_{99}$ |
| --- | --- | --- | --- |
| 1 | μg/mL | 0.001 | NA |
| 2 | μg/mL | 0.0002 | >10 |
| 3 | μg/mL | 0.0002 | >10 |
| 4 | μg/mL | 0.0002 | >10 |
| 5 | μg/mL | 0.0003 | 13.8 |
| 6 | μg/mL | 0.001 | 50.5 |
| 7 | μg/mL | 0.0008 | 27.1 |
| PBTZ169 | μg/mL | 0.0003 | >100 |

NA—not available
H37Rv—BTZ-susceptible wild type strain
NTB1—BTZ-resistant mutant of H37Rv It can clearly be derived from Table 1 above that the compounds of the present invention are more effective against the BTZ-resistant mutant NBT1 than the prior art compound PBTZ169, and are equally effective against H37Rv.

The invention claimed is:

1. A compound of formula (I) or a pharmaceutically acceptable salt thereof:

(I)

wherein
n is 2;
R$^1$ is a linear, branched or cyclic C$_{3-12}$ alkyl group, a linear, branched or cyclic C$_{3-12}$ alkenyl group, a linear, branched or cyclic C$_{3-12}$ alkynyl group, all of which may be substituted with halogen, and wherein one or two CH$_2$-groups may be substituted with O or S,
or

\X-Y-Z-Q, wherein
X is a linear or branched C$_{1-6}$ alkyl group, a linear or branched C$_{1-6}$ alkenyl group, or a linear or branched C$_{1-6}$ alkynyl group;
Y is a direct bond, O, S, NH, NMe, NEt, or NPr;
Z is a direct bond, or a linear or branched C$_{1-3}$ alkyl group;
Q is cyclopentyl, cyclohexyl, cycloheptyl, phenyl, or naphtyl, which may be substituted with 1-3 substituents selected from halogen, a linear or branched C$_{1-3}$ alkoxy group, a linear or branched C$_{1-3}$ alkenyloxy group, a linear or branched C$_{1-3}$ alkynyloxy group, mono-, di or trifluoromethyl; and
R$^2$ is NO$_2$ or NHOH.

2. The compound according to claim 1, wherein R$^1$ is a linear, branched or cyclic C$_{3-12}$ alkyl group, which may substituted with halogen, and wherein one or two CH$_2$-groups may be substituted with O or S.

3. The compound according to claim 1, wherein n is 2, R$^1$ is a linear or cyclic C$_{4-9}$ alkyl group, and R$^2$ is NO$_2$.

4. The compound according to claim 1, which is a hydrochloride salt of formula (Ia):

(Ia)

wherein n, R$^1$ and R$^2$ are as defined in claim 1.

5. A method for treating a bacterial infection, the method comprising administering to a subject in need thereof a compound according to claim 1 or a pharmaceutically acceptable salt thereof, thereby treating said bacterial infection in said subject.

6. A pharmaceutical composition comprising the compound of formula (I) or a pharmaceutically acceptable salt thereof according to claim 1 and a pharmaceutically acceptable excipient.

7. The compound of claim 1, wherein R$^2$ is NO$_2$.

8. The method according to claim 5, wherein the bacterial infection is a mycobacterial infection.

9. The method according to claim 8, wherein the mycobacterial infection causes a disease selected from the group consisting of tuberculosis, buruli ulcer and leprosy.

* * * * *